United States Patent
Markovsky et al.

(10) Patent No.: US 11,119,102 B1
(45) Date of Patent: Sep. 14, 2021

(54) TEST DEVICE, METHOD, AND ASSEMBLY

(71) Applicant: Charm Sciences, Inc., Lawrence, MA (US)

(72) Inventors: Robert J Markovsky, Brentwood, NH (US); Cody Thiboult, Candia, NH (US)

(73) Assignee: Charm Sciences, Inc., Lawrence, MA (US)

( * ) Notice: Subject to any disclaimer, the term of this patent is extended or adjusted under 35 U.S.C. 154(b) by 701 days.

(21) Appl. No.: 15/434,399

(22) Filed: Feb. 16, 2017

Related U.S. Application Data

(60) Provisional application No. 62/420,697, filed on Nov. 11, 2016, provisional application No. 62/413,041, filed on Oct. 26, 2016, provisional application No. 62/295,733, filed on Feb. 16, 2016.

(51) Int. Cl.
| | |
|---|---|
| *G01N 33/558* | (2006.01) |
| *G01N 33/543* | (2006.01) |
| *G01N 33/58* | (2006.01) |
| *G01N 33/553* | (2006.01) |

(52) U.S. Cl.
CPC ..... *G01N 33/558* (2013.01); *G01N 33/54313* (2013.01); *G01N 33/54386* (2013.01); *G01N 33/585* (2013.01); *G01N 33/553* (2013.01)

(58) Field of Classification Search
CPC ............... G01N 33/558; G01N 33/585; G01N 33/54313; G01N 33/54386; G01N 33/553; B01L 2300/0825
USPC ..... 422/400, 401, 420, 425, 430; 435/287.7, 435/287.9, 970, 805, 810; 436/169, 514, 436/518, 530, 810
See application file for complete search history.

(56) References Cited

U.S. PATENT DOCUMENTS

| | | | |
|---|---|---|---|
| 4,540,659 A | 9/1985 | Litman et al. | 435/7 |
| 4,700,714 A | 10/1987 | Fuisz | 128/767 |
| 4,703,017 A | 10/1987 | Campbell et al. | 436/501 |
| 4,743,560 A | 5/1988 | Campbell et al. | 436/501 |
| 4,826,759 A | 5/1989 | Guire et al. | 435/4 |
| 4,999,285 A | 3/1991 | Stiso | 438/7.9 |
| 5,158,869 A | 10/1992 | Pouletty et al. | 435/7.9 |
| 5,179,005 A | 1/1993 | Phillips et al. | 435/14 |
| 5,208,535 A | 5/1993 | Nakayama et al. | 324/318 |
| 5,229,073 A | 7/1993 | Luo et al. | 422/56 |
| 5,238,652 A | 8/1993 | Sun et al. | 422/61 |
| 5,260,222 A | 11/1993 | Patel et al. | 436/180 |
| 5,266,497 A | 11/1993 | Imai et al. | 436/514 |
| 5,296,347 A | 3/1994 | Lamotte, III | 435/5 |
| 5,356,782 A | 10/1994 | Moorman et al. | 435/7.9 |
| 5,395,754 A | 3/1995 | Lambotte et al. | 435/607.4 |
| 5,434,053 A | 7/1995 | Piasio | 435/79 |
| 5,451,504 A | 9/1995 | Fitzpatrick et al. | 435/7.2 |
| 5,521,102 A | 5/1996 | Boehringer et al. | 436/523 |
| 5,541,059 A | 7/1996 | Chu | 435/5 |
| 5,541,069 A | 7/1996 | Mortensen et al. | 435/7.9 |
| 5,545,721 A | 8/1996 | Carroll et al. | 530/391.7 |

(Continued)

*Primary Examiner* — Christopher L Chin
(74) *Attorney, Agent, or Firm* — MacCord Mason PLLC

(57) ABSTRACT

Test strip devices, assemblies, systems, and methods for the analysis of a sample are shown and described. In one embodiment, a test strip includes a nitrocellulose membrane, a filtration conjugate pad with a fibrous labeled receptor bottom side, and an overlay tape enclosing the nitrocellulose membrane and a portion of the filtration conjugate pad. An assembly may include a delivery device for delivering sample to the test strip.

12 Claims, 6 Drawing Sheets

(56) References Cited

U.S. PATENT DOCUMENTS

| | | | |
|---|---|---|---|
| 5,565,502 A | 10/1996 | Glimcher et al. | 436/180 |
| 5,585,241 A | 12/1996 | Lindmo | 435/6 |
| 5,591,645 A | 1/1997 | Rosenstein | 436/514 |
| 5,602,040 A | 2/1997 | May et al. | 436/514 |
| 5,622,871 A | 4/1997 | May et al. | 436/514 |
| 5,648,274 A | 7/1997 | Chandler | 436/514 |
| 5,656,448 A | 8/1997 | Kang et al. | 435/7.94 |
| 5,712,172 A | 1/1998 | Huang et al. | 436/518 |
| 5,714,389 A | 2/1998 | Charlton et al. | 436/514 |
| 5,726,010 A | 3/1998 | Clark | 435/5 |
| 5,726,013 A | 3/1998 | Clark | 435/5 |
| 5,739,041 A | 4/1998 | Nazareth et al. | 436/518 |
| 5,753,517 A | 5/1998 | Brooks et al. | 436/514 |
| 5,766,962 A | 6/1998 | Childs et al. | 436/518 |
| 5,780,308 A | 7/1998 | Ching et al. | 436/514 |
| 5,939,272 A | 8/1999 | Buechler et al. | 435/7.1 |
| 5,962,339 A | 10/1999 | Midgely | 436/534 |
| 5,985,675 A | 11/1999 | Charm et al. | 436/514 |
| 6,001,658 A | 12/1999 | Fredrickson | 436/514 |
| 6,121,008 A | 9/2000 | Fitzpatrick et al. | 435/7.9 |
| 6,177,281 B1 | 1/2001 | Manita | 436/518 |
| 6,258,323 B1 | 7/2001 | Hormann et al. | 422/99 |
| 6,281,004 B1 | 8/2001 | Bogen et al. | 435/287.1 |
| 6,319,466 B1 | 11/2001 | Markovsky et al. | 422/56 |
| 6,368,876 B1 | 4/2002 | Huang et al. | 436/518 |
| 6,475,805 B1 | 11/2002 | Charm et al. | 436/514 |
| 6,509,196 B1 | 1/2003 | Brooks et al. | 436/514 |
| 6,656,744 B2 | 12/2003 | Pronovost et al. | 436/514 |
| 6,699,722 B2 | 3/2004 | Bauer et al. | 436/518 |
| 7,410,808 B1 | 8/2008 | Saul et al. | 436/514 |
| 7,863,057 B2 | 1/2011 | Saul et al. | 436/518 |
| 10,289,089 B2 | 5/2019 | Kirsamer et al. | 435/100 |
| 2003/0049857 A1 | 3/2003 | Chan | 436/170 |
| 2003/0162236 A1 | 8/2003 | Harris et al. | 435/7.92 |
| 2003/0199004 A1 | 10/2003 | Fong | 435/7.9 |
| 2004/0002063 A1 | 1/2004 | Chan et al. | 435/5 |
| 2004/0002165 A1 | 1/2004 | Buchannan et al. | 436/180 |
| 2004/0161859 A1 | 8/2004 | Guo et al. | 436/514 |
| 2004/0171092 A1 | 9/2004 | Harris et al. | 435/7.92 |
| 2004/0241750 A1 | 12/2004 | Nordman et al. | 435/7.1 |
| 2004/0241882 A1 | 12/2004 | DiNello et al. | 436/518 |
| 2007/0224701 A1* | 9/2007 | Rosenstein | G01N 33/558 436/514 |

* cited by examiner

TEST DEVICE, METHOD, AND ASSEMBLY

This application claims the benefit of U.S. Provisional application No. 62/295,733, filed Feb. 16, 2016; U.S. Provisional application No. 62/413,041, filed Oct. 26, 2016; and U.S. Provisional application No. 62/420,697, filed Nov. 11, 2016, all of which are herein incorporated by reference.

FIELD OF THE TECHNOLOGY

The present disclosure relates generally to binding assays, and more particularly to improved test devices and assemblies.

BACKGROUND

Various types of testing apparatuses may detect the presence of one or more analytes in a sample. Onsite testing tools may be preferable for certain tasks, such as detecting contaminants in food supplies at a farm and the like. However, conventional systems and methods limit onsite applicability. For instance, many current applications fail to provide rapid analysis without long incubations or tedious preparation. In addition, loading a sample onto the testing apparatus without relying on other accessories/additional steps would be beneficial for numerous onsite testing scenarios.

Therefore, Applicant desires systems and methods for performing binding assays to improve onsite testing without the drawbacks presented by traditional systems and methods.

SUMMARY

In accordance with the present disclosure, test strips and systems are provided for the analysis of a sample. This disclosure provides improved lateral flow devices and methods that are convenient, efficient, and safe for the user, particularly when used to detect the presence or absence of an analyte in a sample.

One embodiment of the present disclosure includes a test strip having a solid backing support; a nitrocellulose membrane adhered to the solid backing support and including at least one control area and at least one test area; a filtration conjugate pad having a top side and a fibrous bottom side and aligned to the nitrocellulose membrane at a contact point, and wherein the bottom fibrous side includes a labeled receptor; and an overlay enclosing the nitrocellulose membrane and the contact point between the nitrocellulose membrane and filtration conjugate pad.

In some examples, the overlay comprises a transparent tape laminated onto the test strip to prevent contamination and drive sample flow along the test strip. For instance, the overlay may be aligned over the filtration conjugate pad to generally define an exposed filtration conjugate pad segment and a concealed filtration conjugate pad segment. For example, the overlay may be aligned over substantially half of the filtration conjugate pad. Further, the overlay may pressurize at least a portion of the test strip to generate an even flow of sample about the test strip.

In particular examples, bead labeled receptors are sprayed to the fibrous bottom of the filtration conjugate pad, and capillary action of the sample traverses sample to the bead labeled receptors. Typically, the capillary action of the sample solubilizes the bead labeled receptors. Advantageously, sample does not contact the bead labeled receptors prior to the capillary action of the sample during travel along the test strip.

In some examples, the contact point includes an overlap of filtration conjugate pad onto the nitrocellulose membrane. For instance, the contact point includes between about two millimeters to about three millimeters of overlap of filtration conjugate pad onto the nitrocellulose membrane.

Typically, the solid support comprises a transparent material for directly viewing a result without equipment. In particular examples, the filtration conjugate pad includes a fiberglass pad or the like. The nitrocellulose membrane may include a plurality of control lines. Similarly, the nitrocellulose membrane may include a plurality of test lines. Further, the labeled receptors may be antibodies conjugated to colloidal gold particles.

Another embodiment of the disclosure is a method for analyzing a liquid sample for a presence of one or more analytes of placing an end of a test strip having an adjacent labeled receptor adhered to a bottom fibrous side of a filtration conjugate pad directly into the liquid sample, the test strip configured to traverse lateral flow of the liquid sample; allowing the liquid sample to solubilize the labeled receptor to form a mobile phase, the labeled receptor characterized by an ability to fowl an analyte-receptor complex when an analyte is present within the liquid sample; allowing the mobile phase to flow to at least one test line, the at least one test line comprising a test line capture agent immobilized on the test strip, the test line capture agent characterized in that the capture agent has greater binding affinity to the labeled receptor than the analyte-receptor complex; and allowing the mobile phase to flow to at least one control line, the control line comprising a control line capture agent, the control line capture agent characterized in that the affinity to the labeled receptor is equivalent to the affinity to the analyte-receptor complex.

In some examples, the method includes comparing intensity of a detectable signal at each of the test line and the control line, wherein a greater intensity of the detectable signal in any one test line as compared to the control line indicates a negative result for a particular analyte and a greater intensity of the detectable signal in the control line compared to any one test line indicates a positive result for the particular analyte. Typically, comparing intensity of the detectable signals includes directly observing the test strip without equipment. Further, the method may include adjusting test sensitivity by adding a mixture of receptors to the test strip.

Yet another embodiment of the disclosure includes an assembly for the analysis of a sample, the assembly may include any of the test strip embodiments and examples shown and described herein and the delivery device embodiments and examples shown and described herein. For instance, the test strip may have a nitrocellulose membrane, a filtration conjugate pad overlapping a portion of the nitrocellulose membrane and including a fibrous bottom side with a sprayed bead labeled receptor, and an overlay tape enclosing the nitrocellulose membrane and a portion of the filtration conjugate pad; and the delivery device may have an elongated body and a receiving distal cavity comprising a surface tension to retain a predetermined volume of the sample during operation.

Yet another embodiment of the present disclosure includes a delivery device, or the like, for the analysis of a sample having an elongated body; and a receiving distal end having a cavity to receive the sample, wherein the cavity comprising a surface tension adapted to retain a predetermined volume of the sample during operation.

In some examples, the elongated body has a handle. The elongated body may have a length between about one half inch to about four inches, for instance of about two inches. The cavity may include a plastic material adapted to retain a predetermined volume of a dairy sample during operation. The predetermined volume may include about three hundred milliliters of a dairy sample. The predetermined volume may be independent of a sample film residue.

In other examples, the cavity may include an outer layer adapted to retain a predetermined volume of a dairy sample during operation. The predetermined volume comprising about three hundred milliliters of a dairy sample. The predetermined volume may be independent of a sample film residue. The receiving end may include a width adapted to traverse a test vial.

In another embodiment of the disclosure, an assembly for the analysis of a sample includes a scoop spoon having an elongated end and an opposing receiving end adapted to protrude the sample and retain a volume of the sample independent of a film residue.

In some examples, the scoop spoon has a cavity with a surface tension adapted to retain a predetermined volume of the sample. The sample may include a dairy sample. The sample may include a milk sample. The scoop spoon may include a handle. The scoop spoon may include an elongated body with a length between about one half inch to about four inches, for instance about two inches.

In particular examples, the receiving end comprises a material adapted to retain a predetermined volume of a dairy sample during operation. The predetermined volume may include about three hundred milliliters of a dairy sample. In other examples, the receiving end may have an outer layer adapted to retain a predetermined volume of a dairy sample during operation. The predetermined volume may include about three hundred milliliters of a dairy sample. Further, the receiving end typically includes a width adapted to fit within a test vial.

In certain examples, the assembly includes a solid support, or the like, having a top side and a bottom side. A nitrocellulose membrane may be adhered to the bottom side of the solid support. A filtration conjugate pad may have a first side and a second side, the first side of the filtration conjugate pad adhered to a portion of a nitrocellulose membrane and including labeled receptors between the filtration conjugate pad and the nitrocellulose membrane.

In alternative examples, an absorbent sponge is adhered onto the bottom side of the solid support at an end, the absorbent sponge directing flow of the sample from the opposing end. A clear plastic overlay tape may be applied over the absorbent sponge and the nitrocellulose membrane and at least a portion of the filtration conjugate pad, wherein the clear plastic overlay tape prevents contamination. Further, a clear plastic overlay tape may be applied over the absorbent sponge and the nitrocellulose membrane and at least a portion of the filtration conjugate pad, wherein the clear plastic overlay tape pressurizes at least a portion of the test strip to generate an even flow of substrate about the test strip.

In certain examples, the solid support is comprised of a plastic, for instance polystyrene. The solid support may include a transparent material for directly viewing a test result without equipment. The first side of the filtration conjugate pad may be fibrous and the second side of the filtration conjugate pad is checkered. For instance, the filtration conjugate pad may be a fiberglass pad, or similar membrane.

Yet another embodiment of the present disclosure includes a lateral flow test strip for the analysis of a sample having a solid support, nitrocellulose membrane, filtration conjugate pad, and absorbent sponge. The solid support has a top side and a bottom side. The nitrocellulose membrane is generally adhered to the bottom side of the solid support. The filtration conjugate pad has a first side and a second side, and the first side of the filtration conjugate pad is adhered to a portion of the nitrocellulose membrane and includes labeled receptors between the filtration conjugate pad and the nitrocellulose membrane. In alterative examples, the absorbent sponge is generally adhered onto the bottom side of the solid support at an end of the test strip, thus the absorbent sponge generally directs flow of the sample from the opposing end of the test strip.

In one example, the solid support is comprised of a plastic. For instance, the plastic may be polystyrene. Further, the solid support may comprise a transparent material for directly viewing the results without equipment.

In certain examples, the first side of the filtration conjugate pad is fibrous and the second side of the filtration conjugate pad is checkered. The filtration conjugate pad may comprise a fiberglass pad, or similar membrane. Further, the nitrocellulose membrane includes at least one test line and at least one control line. However, those of ordinary skill in the art having the benefit of this disclosure will recognize any number of corresponding test lines and control lines for a particular test.

In some examples, the labeled receptors are antibodies conjugated to colloidal gold particles. In one example, a clear plastic overlay tape applied over the absorbent sponge and the nitrocellulose membrane and at least a portion of the filtration conjugate pad, wherein the clear plastic overlay tape prevents contamination. Further, the clear plastic overlay tape may pressurize at least a portion of the test strip to generate an even flow of substrate about the test strip.

In another embodiment, a method for analyzing a liquid sample for a presence of one or more analytes includes placing an end of a test strip having a labeled receptor directly into the liquid sample, the test strip configured to traverse lateral flow of the liquid sample; allowing the liquid sample to contact the labeled receptor to form a mobile phase, the labeled receptor characterized by an ability to form an analyte-receptor complex when an analyte is present within the liquid sample; allowing the mobile phase to flow to at least one test line, the at least one test line comprising a test line capture agent immobilized on the test strip, the test line capture agent characterized in that the capture agent has greater binding affinity to the labeled receptor than the analyte-receptor complex; allowing the mobile phase to flow to at least one control line, the control line comprising a control line capture agent, the control line capture agent characterized in that the affinity to the labeled receptor is equivalent to the affinity to the analyte-receptor complex; and measuring the intensity of the detectable signal at each of the at least one test line and the control line, wherein a greater intensity of the detectable signal in any one test line as compared to the control line indicates a negative result for a particular analyte and a greater intensity of the detectable signal in the control line compared to any one test line indicates a positive result for the particular analyte.

In certain examples, the method includes adjusting test sensitivity by adding a mixture of receptors to the test strip. Further, the method may include measuring the intensity of the detectable signal includes directly observing the test strip without equipment. The labeled receptor may comprise an antibody conjugated to a colloidal gold particle. The test line capture agent may comprise a representative analyte or analog thereof.

In some examples, the method includes placing the test strip in an incubator after placing the end of the test strip directly into the liquid sample, and removing the test strip from the incubator prior to directly observing the test strip.

In yet another embodiment of the present disclosure, a lateral flow test strip for analysis of a liquid sample includes a plastic backing having a top side and a bottom side; a nitrocellulose membrane adhered to the bottom side of the plastic backing; a filtration conjugate pad having a checkered side and a fibrous side, the fibrous side of the filtration conjugate pad adhered to a portion of the nitrocellulose membrane and including bead-labeled receptors between the filtration conjugate pad and the nitrocellulose membrane; and an absorbent sponge adhered onto the bottom side of the plastic backing at an end of the test strip, the absorbent sponge directing flow of the liquid sample from the opposing end of the test strip.

The above summary was intended to summarize certain embodiments of the present disclosure. Embodiments will be set forth in more detail in the figures and description of embodiments below. It will be apparent, however, that the description of embodiments is not intended to limit the present inventions, the scope of which should be properly determined by the appended claims.

BRIEF DESCRIPTION OF THE DRAWINGS

Embodiments of the disclosure will be better understood by a reading of the Description of Embodiments along with a review of the drawings, in which.

DESCRIPTION OF EMBODIMENTS

Figure 1A:
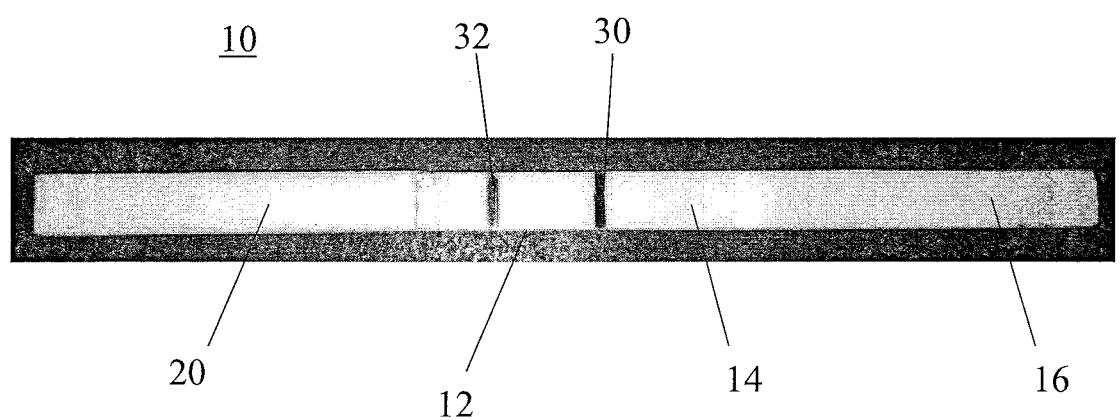
FIG. 1A is an overhead view of a test strip according to an embodiment of the disclosure.

In the following description, like reference characters designate like or corresponding parts throughout the several views. Also in the following description, it is to be understood that such terms as "forward," "rearward," "left," "right," "upwardly," "downwardly," and the like are words of convenience and are not to be construed as limiting terms.

Figure 1B:
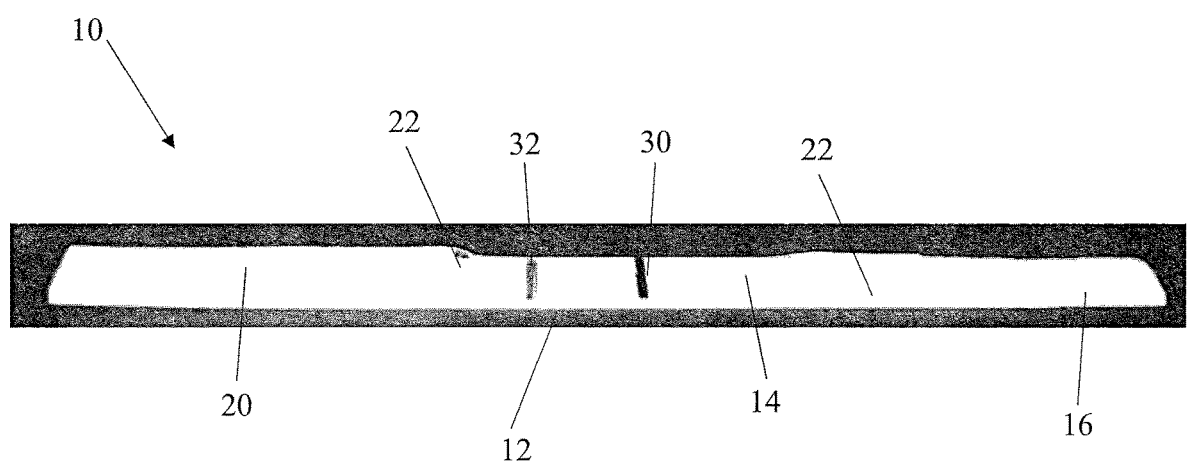
FIG. 1B is a side view of a test strip according to FIG. 1A, assembled according to one example of the disclosure.
Figure 2A:
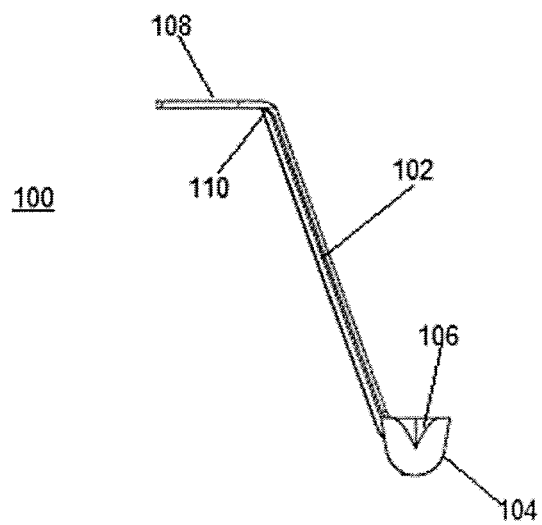
FIG. 2A is a side perspective view of a sample delivery device according to an embodiment of the disclosure.
Figure 2B:
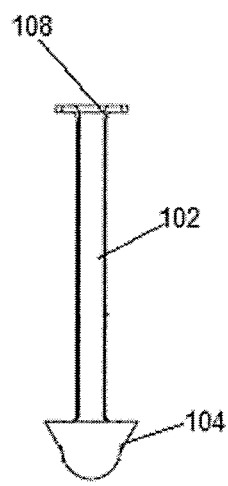
FIG. 2B is a front view of the embodiment introduced in FIG. 2A.
Figure 2C:
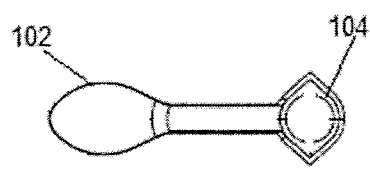
FIG. 2C is a top view of the embodiment introduced in FIG. 2A.

Referring now to the drawings in general, and FIGS. 1A and 2A in particular, it will be understood that the illustrations are for the purpose of describing embodiments of the disclosure and are not intended to limit the disclosure or any invention thereto. As best seen in FIGS. 1A and 1B, test strip 10 includes a solid support 12 with a membrane 14, a filtration conjugate pad 16 adjacent to the nitrocellulose 14, and an overlay 22. Typically, the filtration conjugate pad 16 includes at least one fibrous face to receive beads as shown and described herein. Particular embodiments of the assembly may include a delivery device, for instance as introduced in FIGS. 2A-2C, for delivering a predetermined volume, depth, or similar arrangement of liquid sample to the test strip 10.

Test strip 10 detects one or more substances (i.e. analytes and the like) in a sample, including a liquid sample or the like. Typically, an end of test strip 10 is dipped directly into a sample, and the liquid sample begins traveling toward the other end of the test strip. If an analyte is present within the sample, it will bind to a labeled receptor. Depending on the concentration of analytes within the sample, a portion of labeled receptor may remain unbound yet continue to travel along with the rest of the mobile phase. As the mobile phase flows from one end to the other, at least a portion of unbound labeled receptors will be captured at a test zone. The remaining bound and unbound labeled receptors will be captured at a control zone, and presence of analytes can be determined by comparing signal intensities between a test zone and a control zone. A higher intensity at a test zone generally indicates a negative result (i.e., absence of analyte) whereas a higher intensity at a control zone indicates a positive result (i.e., presence of analyte).

Solid support 12 provides a structural foundation for test strip 10 wherein any of the various strip components shown and described herein may be attached. Solid support 12 may be comprised of any combination of plastics, such as polystyrene. In one example, solid support 12 is a transparent plastic material which may be useful for observing results by reading the transmission through test strip 10 rather than measuring the reflectance on the top of test strip 10.

A membrane, for instance a nitrocellulose membrane 14, is adhered to at least one side of solid support 12. Nitrocellulose membrane 14 enables the mobile phase to flow from one end of test strip 10 towards the direction of the opposing end. In particular examples, nitrocellulose membrane 14 includes beads, and the membrane 14 containing the beads may be pretreated with a blocking solution. The blocking solution may dissolve when the diluted sample is added to the apparatus. Similarly, the nitrocellulose membrane can also be pretreated and/or blocked.

Nitrocellulose membrane 14 may further include a stationary phase comprising at least one test line 30 and at least one control line 32. Test line 30 includes a capture agent adapted for binding to labeled receptor that is not bound to analyte. In particular examples, the test line capture agent comprises a representative analyte or analog thereof. Typically, control line 32 is used for comparison to at least one, or more, test lines 30. Further, control line 32 may signal that the test functioned properly and/or is complete. In particular embodiments, control line 32 includes a substance, such as a control line capture agent that has affinity to both labeled receptor unbound by analyte from the sample and the labeled receptor bound by analyte from the sample.

In some embodiments, the control line capture agent includes a capture agent with affinity to the antibody attached to an antispecies antibody on the protein A. In particular examples, the control line capture agent is cloxacillin that is bound to the test strip 10 using BSA, and the antibody attached to the anti-species antibody is an antibody to cloxacillin. Some useful antibody binding proteins include protein A, protein G or protein AG and recombinant forms of the same. Further, when analyte receptor, discussed hereinafter, is an antibody, or fragments thereof, the capture agents can include antigens with an affinity to the antibody.

For instance, antigens include analogues thereof, or any substance exhibiting affinity to the receptor that is similar to that of the analyte.

A filtration conjugate pad 16 is adhered adjacent to the nitrocellulose membrane 14, for instance toward the end of test strip 10 where a liquid sample may later be applied (i.e., the application end). Filtration conjugate pad 16 includes a first side and a second side, wherein the first side is adhered onto test strip 10. Portions of filtration conjugate pad 16 that are not adhered to nitrocellulose membrane 14 may be adhered to solid support 12. Filtration conjugate pad 16 may be comprised of a cellulosic material, fiberglass pad, membrane or the like. In particular examples, the first side of filtration conjugate pad 16 may be fibrous and the second side of filtration conjugate pad 16 may be checkered. Applicants have discovered unexpected advantages of adhering, including spraying, bonding, and the like, beads on the fibrous portion for enhanced consistent line development as shown and described herein.

In certain examples, the labeled receptors may be found in an area of filtration conjugate pad 16 overlapping nitrocellulose membrane 14. As discussed herein, labeled receptors are responsible for binding analyte present within a liquid sample. In some examples, labeled receptors are comprised of antibodies bound to bead-based labels. Bead-based labels may include chromogens, such as colloidal gold particles or other chemiluminescent metals. Buffers may be used to enhance the sensitivity of labeled receptors. In alternative examples, an absorbent sponge may be adhered onto solid support 12 toward an opposing end away from filtration conjugate pad 16. The absorbent sponge may include a region overlapping nitrocellulose membrane 14. Once the sample is applied to test strip 10, the mobile phase flows towards absorbent sponge. The mobile phase, along with any remaining labeled receptors that are not bound to the stationary phase, may be absorbed by an absorbent sponge.

As best seen in FIG. 1A, test strip 10 may further include a covering 22 overlaying at least a portion of the strip. For example, covering 22 may be a clear plastic overlay tape aligned over the nitrocellulose membrane 14 and at least a portion of filtration conjugate pad 16. Covering 22 may prevent contamination from entering the mobile and/or stationary phases. Moreover, covering 22 may also evenly regulate the flow of the mobile phase by generating pressure on at least a portion of test strip 10 as shown and described herein.

Any of the test strips herein may be dipped, partially submerged, and in certain alternative examples fully submerged, or the like into a sample delivery device to enhance testing efficiency and minimize contamination. One example of a delivery device is introduced in FIGS. 2A-2C, wherein the delivery device 100 may include a receiving end 104 and an operating end 102, for instance a handle or the like. The receiving end 104 may include a cavity 106. The cavity 106 may include any shape and elongation, for instance any number of sides, either rounded or squared, with an open face to receive and retain any of the samples shown and described herein. In operation, a sample is applied to test strip 10 by dipping the receiving distal end 106 into the sample to retain a predetermined amount of sample as shown and described herein. As shown in FIG. 2A, the delivery device 100 generally has an elongated body 102 separating a handling end 108 and an opposing receiving distal end 104. As illustrated, the receiving distal end 104 includes cavity 106 having a surface tension to retain a predetermined volume of sample during operation as illustrated and noted herein to provide the unexpected advantages. In particular examples, an elbow 110, or the like, offsets the handling end 108 and the opposing receiving distal end 104. Other examples include any variety of elongated, angled, or additional offset arrangements to space the handling end 108 and receiving distal end 104 as understood by those skilled in the art having the benefit of this discourse.

Figure 3:
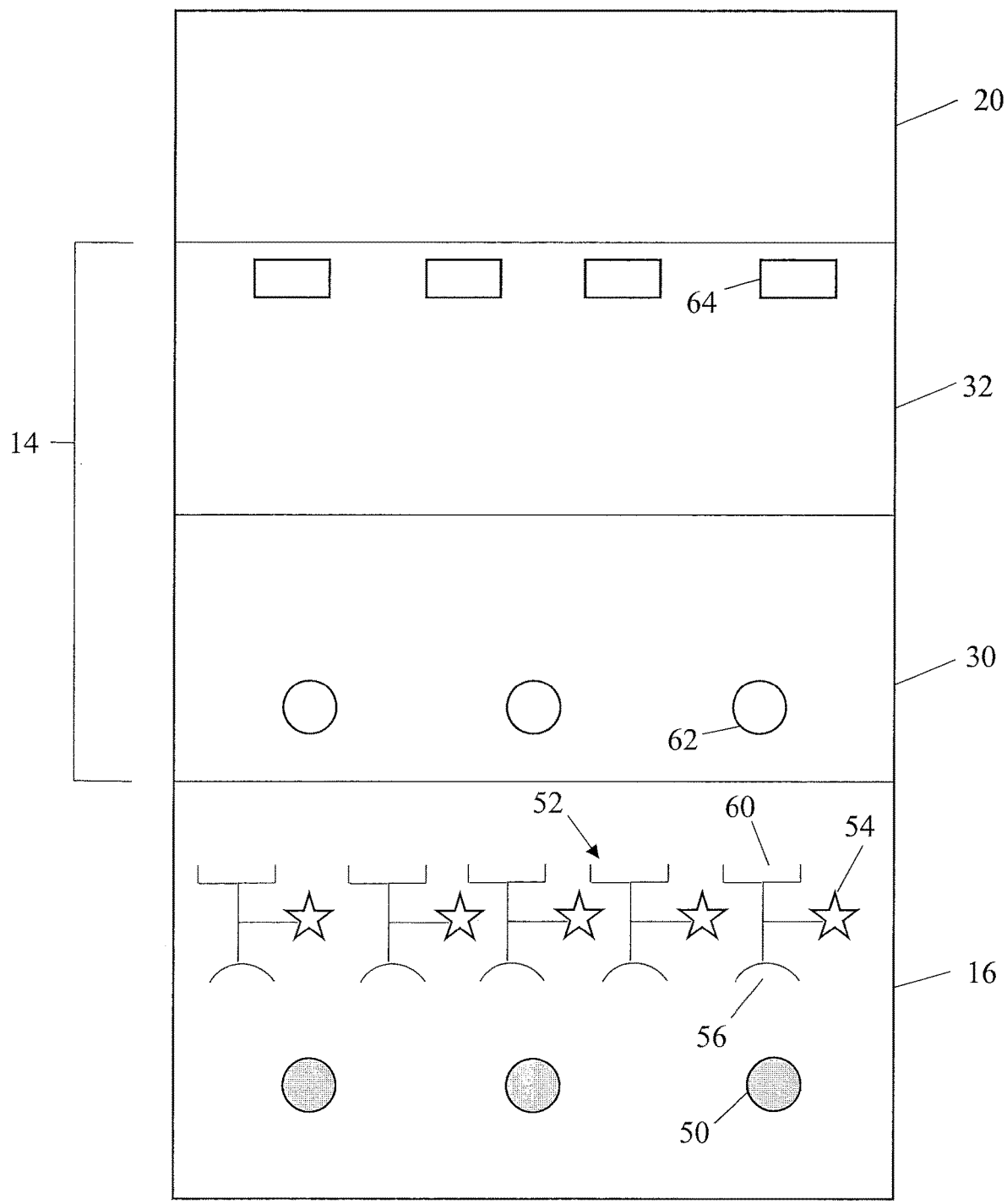
FIG. 3 is an isolated schematic view of one example of test strip components introduced in the embodiment of FIG. 1A, showing the initial application of sample.
Figure 4:
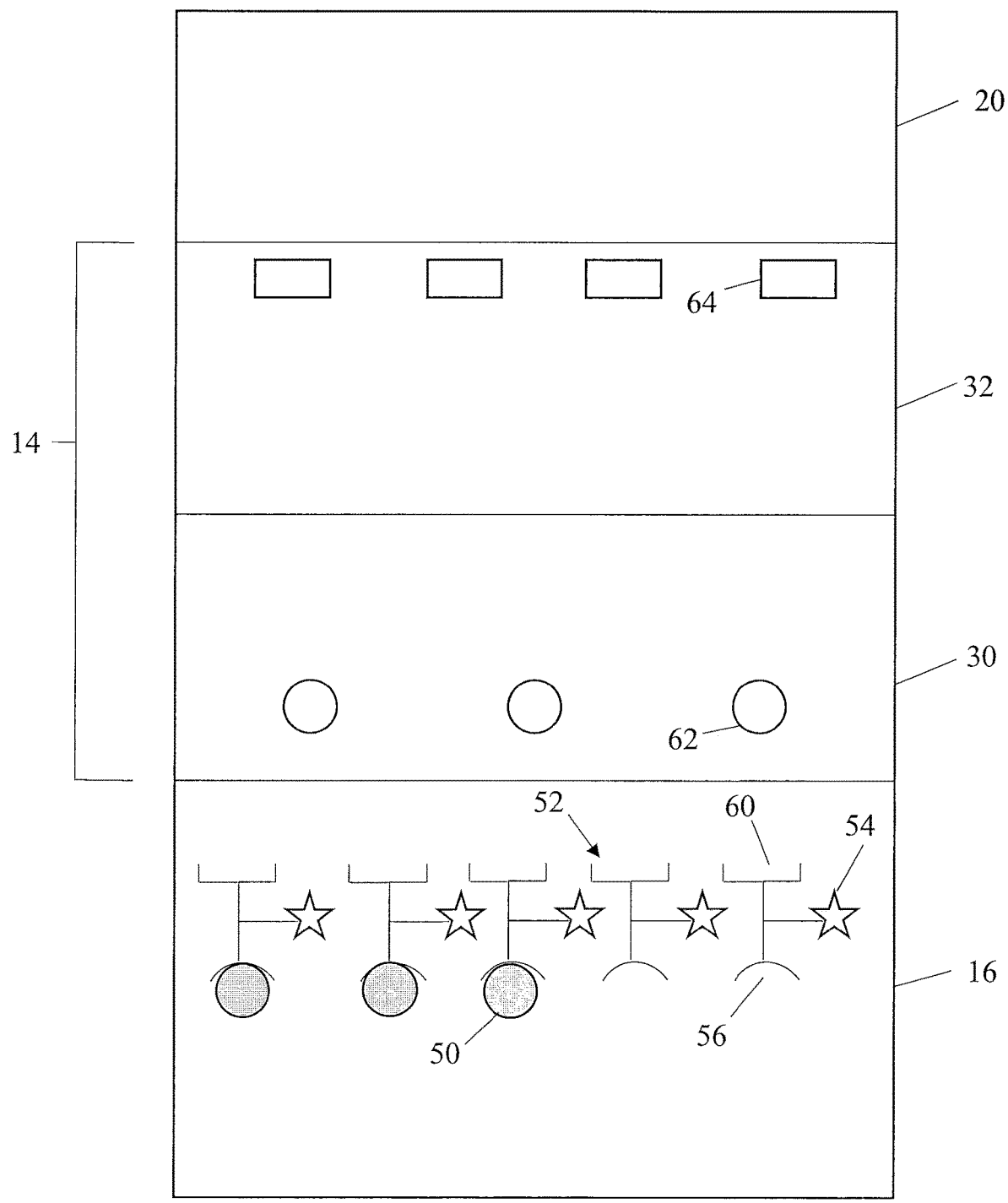
FIG. 4 is an isolated schematic view of one example of test strip components introduced in the embodiment of FIG. 1A, showing binding of analytes within sample to labeled receptors.

Additionally, those of ordinary skill will recognize additional sample applications, including but not limited to diluting solid, semi-solid samples and the like. Turning to FIG. 3, as the liquid sample makes contact with filtration conjugate pad 16, the sample and accompanying analytes 50 (if present) begins flowing toward the other end of the test strip through any of the elements shown and described herein, including but not limited to via capillary action. The sample then mixes with labeled receptors 52 as the mobile phase traverses through filtration conjugate pad 16. Labeled receptors 52 include a label 52, an analyte binding site 56, and a secondary binding site 60. As seen in FIG. 4, if an analyte 50 is present within the sample, it will bind to a labeled receptor 52 at the analyte binding site 56 to form an analyte-receptor complex. Depending on the concentration of analytes within the liquid sample, a portion of labeled receptor 52 may remain unbound yet continue to travel along with the rest of the mobile phase. The mobile phase continues to flow toward the stationary phase of membrane 14.

Figure 5:
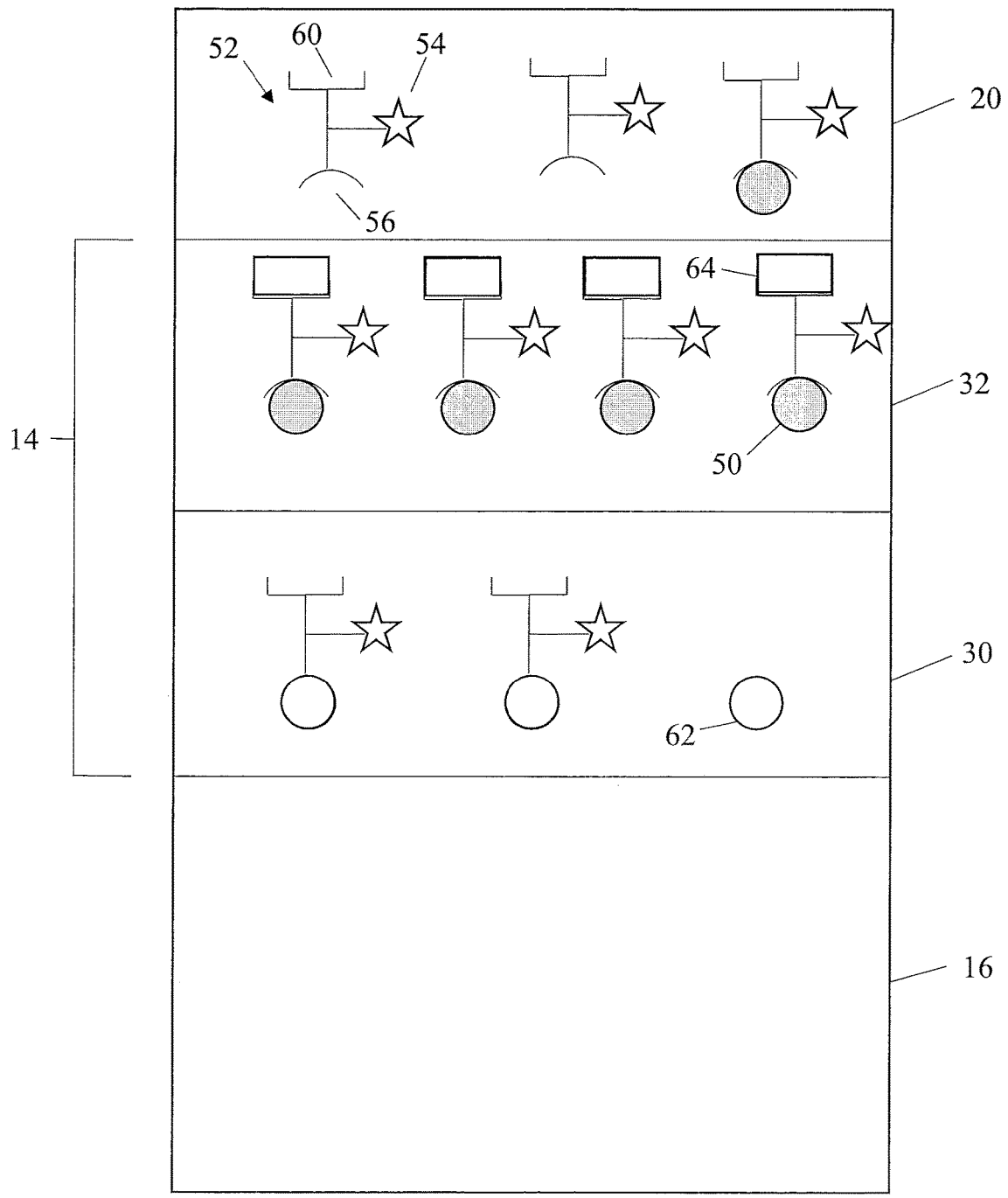
FIG. 5 is an isolated schematic view of one example of test strip components introduced in the embodiment of FIG. 1A, showing a completed binding assay.

FIG. 5 shows an embodiment of test strip components after a completed assay. At least a portion of unbound labeled receptors are captured by test zone capture agents 62 at one or more test zones 30 within membrane 14. Capture agents 62 at test zone 30 are characterized by their greater affinity toward labeled receptor as opposed to analyte-receptor complexes. Bound and unbound labeled receptors that are not captured by test zones 30 may be captured by capture agents 64 at one or more control zones 32 located closer toward the opposing end of the application end. The binding affinities for the labeled receptor as well as the analyte-receptor complex are equivalent for the capture agents at control zone 32.

The remaining mobile phase, including all bound and unbound labeled receptors not captured at either test zone 30 or control zone 32. In alternative examples, the mobile phase may be absorbed by absorbent sponge. Depending on the label 54 conjugated to the receptors, presence of analytes 50 may be determined by directly comparing signal intensities between test zones 30 and control zones 32 with no additional equipment needed to observe the signals. In some examples, additional equipment may be used to conduct assays. For instance, an incubator may be used to control and/or stabilize the temperature where applicable.

A higher intensity at a test zone generally indicates a negative result (i.e., absence of analyte) whereas a higher intensity at a control zone indicates a positive result (i.e., presence of analyte). In some examples, a false negative result may be caused by low sensitivity or low concentration of analyte. Similarly, a false positive result may be caused by oversensitive or unspecific binding to substances within the sample. Test sensitivity may be further adjusted by adding a mixture of additional receptors to the test strip.

Numerous characteristics and advantages have been set forth in the foregoing description, together with details of structure and function. Many of the novel features are pointed out in the appended claims. The disclosure, however, is illustrative only, and changes may be made in detail, especially in matters of shape, size, and arrangement of parts, within the principle of the disclosure, to the full extent indicated by the broad general meaning of the terms in which the general claims are expressed. It is further noted that, as used in this application, the singular forms "a," "an," and "the" include plural referents unless expressly and unequivocally limited to one referent.

We claim:

1. A lateral flow test strip for the analysis of a sample, said test strip comprising:
   a. a solid backing support;
   b. a nitrocellulose membrane adhered to said solid backing support and including at least one control area and at least one test area;
   c. a filtration conjugate pad having a top side and a fibrous bottom side and aligned to said nitrocellulose membrane at a contact point, and wherein said bottom fibrous side includes a labeled receptor, and wherein said contact point includes between at least about two millimeters to about three millimeters of an overlap of said filtration conjugate pad onto said nitrocellulose membrane; and
   d. an overlay aligned over said nitrocellulose membrane and said contact point between said nitrocellulose membrane and filtration conjugate pad.

2. The lateral flow test strip of claim 1, wherein said overlay comprises a transparent tape laminated onto said test strip to conceal and aligned substantially parallel to said nitrocellulose membrane and said contact point between said nitrocellulose membrane and filtration conjugate pad to prevent contamination and to apply pressure at pressure points to drive sample flow along said test strip.

3. The lateral flow test strip of claim 2, wherein said overlay aligned over substantially half of said filtration conjugate pad.

4. The lateral flow test strip of claim 1, including a plurality of bead labeled receptors sprayed onto said fibrous bottom of said filtration conjugate pad, and wherein capillary action traverses sample to said bead labeled receptors.

5. The lateral flow test strip of claim 4, wherein said capillary action of said sample solubilizes said bead labeled receptors.

6. The lateral flow test strip of claim 5, wherein said bead labeled receptors aligned along said test strip in a position so that sample does not contact said bead labeled receptors prior to said capillary action when exposed to a predetermined volume of sample.

7. The lateral flow test strip of claim 1, wherein said overlay pressurizes alignment segments along said nitrocellulose membrane to generate an even flow of sample about said test strip.

8. The lateral flow strip of claim 1, wherein said solid support comprises a transparent material for directly viewing a result without equipment.

9. The lateral flow strip of claim 1, wherein said filtration conjugate pad includes a fiberglass pad.

10. The lateral flow strip of claim 1, wherein said nitrocellulose membrane includes a plurality of control lines.

11. The lateral flow strip of claim 1, wherein said nitrocellulose membrane includes a plurality of test lines.

12. The lateral flow strip of claim 1, wherein said labeled receptors are antibodies conjugated to colloidal gold particles.

* * * * *